United States Patent
Bansal et al.

(10) Patent No.: US 10,105,082 B2
(45) Date of Patent: Oct. 23, 2018

(54) METAL-OXIDE-SEMICONDUCTOR CAPACITOR BASED SENSOR

(71) Applicant: International Business Machines Corporation, Armonk, NY (US)

(72) Inventors: Aditya Bansal, Westchester, NY (US); Ashish V. Jagtiani, Westchester, NY (US); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 463 days.

(21) Appl. No.: 14/460,637

(22) Filed: Aug. 15, 2014

(65) Prior Publication Data

US 2016/0045144 A1 Feb. 18, 2016

(51) Int. Cl.
*A61B 5/1486* (2006.01)
*A61B 5/1477* (2006.01)
(Continued)

(52) U.S. Cl.
CPC .......... *A61B 5/1486* (2013.01); *A61B 5/0004* (2013.01); *A61B 5/14507* (2013.01);
(Continued)

(58) Field of Classification Search
CPC . A61B 5/14532; A61B 5/1486; A61B 5/0004; A61B 5/14507; A61B 5/6821;
(Continued)

(56) References Cited

U.S. PATENT DOCUMENTS

| 4,432,937 A | 2/1984 | Kuwayama et al. |
| 4,460,543 A | 7/1984 | Glaeser |

(Continued)

FOREIGN PATENT DOCUMENTS

| EP | 2235773 B1 | 10/2010 |
| GB | 2501801 A | 11/2013 |

(Continued)

OTHER PUBLICATIONS

"A 3-µW CMOS Glucose Sensor for Wireless Contact-Lens Tear Glucose Monitoring" by Liao et al., IEEE Journal of Solid-State Circuits, vol. 47, No. 1, Jan. 2012.*

(Continued)

*Primary Examiner* — Navin Natnithithadha
(74) *Attorney, Agent, or Firm* — Scully, Scott, Murphy & Presser, P.C.; Kristofer Haggerty

(57) ABSTRACT

A glucose sensor comprises a conducting back electrode. The glucose sensor also comprises a silicon substrate in electrical contact with the conducting back electrode. The glucose sensor also comprises a dielectric layer disposed on the silicon substrate. The glucose sensor also comprises a pH sensing layer disposed on the dielectric layer. The glucose sensor also comprises a chemical layer disposed on the pH sensing layer, wherein the chemical layer is in contact with an aqueous solution. The glucose sensor also comprises a conductive electrode disposed on the dielectric layer, where in the conductive electrode is in contact with the aqueous solution.

17 Claims, 5 Drawing Sheets

(51) Int. Cl.
- *G01N 33/84* (2006.01)
- *A61B 5/145* (2006.01)
- *C12Q 1/00* (2006.01)
- *A61B 5/00* (2006.01)
- *G01N 33/52* (2006.01)
- *G01N 27/22* (2006.01)

(52) U.S. Cl.
CPC ........ *A61B 5/14532* (2013.01); *A61B 5/6821* (2013.01); *C12Q 1/006* (2013.01); *G01N 27/221* (2013.01); *G01N 33/528* (2013.01); *G01N 33/84* (2013.01); *A61B 5/1477* (2013.01); *A61B 5/14539* (2013.01); *A61B 2560/0214* (2013.01); *G01N 2333/435* (2013.01); *G01N 2333/90* (2013.01)

(58) Field of Classification Search
CPC .............. A61B 5/14539; A61B 5/1477; A61B 2560/0214; C12Q 1/006; G01N 27/221; G01N 33/528; G01N 33/84; G01N 2333/435; G01N 2333/90
USPC .......................................... 600/309, 345–366
See application file for complete search history.

(56) References Cited

U.S. PATENT DOCUMENTS

| | | |
|---|---|---|
| 4,994,333 A | 2/1991 | Jose et al. |
| 5,240,793 A | 8/1993 | Glaeser |
| 5,306,580 A | 4/1994 | Mansfield, Jr. et al. |
| 5,326,652 A | 7/1994 | Lake |
| 5,339,024 A | 8/1994 | Kuo et al. |
| 5,376,480 A | 12/1994 | Shinoda et al. |
| 5,451,766 A | 9/1995 | Van Berkel |
| 5,558,957 A | 9/1996 | Datta et al. |
| 5,591,548 A | 1/1997 | Mao |
| 5,827,621 A | 10/1998 | Morishita et al. |
| 5,897,522 A | 4/1999 | Nitzan |
| 6,300,929 B1 | 10/2001 | Histake et al. |
| 6,379,835 B1 | 4/2002 | Kucherovsky et al. |
| 6,420,071 B1 | 7/2002 | Lee et al. |
| 6,482,543 B1 | 11/2002 | Shelekhin et al. |
| 6,540,938 B1 | 4/2003 | Afzali-Arkadani et al. |
| 6,652,676 B1 | 11/2003 | Hymer et al. |
| 6,982,132 B1 | 1/2006 | Goldner et al. |
| 7,087,348 B2 | 8/2006 | Holman et al. |
| 7,320,845 B2 | 1/2008 | Zucker |
| 7,348,096 B2 | 3/2008 | Schubert et al. |
| 7,435,395 B2 | 10/2008 | Durkot et al. |
| 7,446,380 B2 | 11/2008 | Bojarczuk, Jr. et al. |
| 7,491,464 B2 | 2/2009 | Merrill et al. |
| 7,531,271 B2 | 5/2009 | Boulton et al. |
| 7,776,468 B2 | 8/2010 | Richards et al. |
| 7,820,329 B2 | 10/2010 | Boulton et al. |
| 8,029,927 B2 | 10/2011 | Tucholski |
| 8,268,475 B2 | 9/2012 | Tucholski |
| 8,441,411 B2 | 5/2013 | Tucholski et al. |
| 8,534,831 B2 | 9/2013 | Tepedino, Jr. et al. |
| 8,586,244 B2 | 11/2013 | Fensore et al. |
| 8,608,310 B2 | 12/2013 | Otis et al. |
| 8,637,349 B2 | 1/2014 | Jenson et al. |
| 8,877,103 B2 | 11/2014 | Alvarez-Carrigan et al. |
| 8,906,088 B2 | 12/2014 | Pugh et al. |
| 9,820,692 B2* | 11/2017 | Wang .................. A61B 5/6833 |
| 2002/0105092 A1 | 8/2002 | Coyle |
| 2002/0161404 A1 | 10/2002 | Schmidt |
| 2003/0099884 A1 | 5/2003 | Chiang et al. |
| 2003/0165744 A1 | 9/2003 | Schubert et al. |
| 2004/0183965 A1 | 9/2004 | Lundgren |
| 2004/0265683 A1 | 12/2004 | Merrill et al. |
| 2005/0048699 A1 | 3/2005 | Matsunami |
| 2005/0079418 A1 | 4/2005 | Kelley et al. |
| 2005/0128409 A1 | 6/2005 | Lee |
| 2005/0244589 A1 | 11/2005 | Kornfield et al. |
| 2005/0266158 A1 | 12/2005 | Pokorny et al. |
| 2006/0115724 A1 | 6/2006 | Buckle et al. |
| 2006/0139540 A1 | 6/2006 | Lu et al. |
| 2006/0292444 A1 | 12/2006 | Chiang et al. |
| 2007/0045106 A1 | 3/2007 | Yang et al. |
| 2007/0138028 A1* | 6/2007 | Chodavarapu ..... G01N 27/4148 205/787.5 |
| 2008/0084498 A1 | 4/2008 | He et al. |
| 2008/0153003 A1 | 6/2008 | Lesaga |
| 2008/0181084 A1 | 7/2008 | Sasabe et al. |
| 2008/0187824 A1 | 8/2008 | Tomantschger |
| 2008/0248382 A1 | 10/2008 | Sastry et al. |
| 2009/0108440 A1 | 4/2009 | Meyer et al. |
| 2010/0003596 A1 | 1/2010 | Sato et al. |
| 2010/0068617 A1 | 3/2010 | Bedjaoui et al. |
| 2010/0285372 A1 | 11/2010 | Lee et al. |
| 2010/0310932 A1 | 12/2010 | Martin et al. |
| 2011/0048781 A1 | 3/2011 | Neudecker et al. |
| 2011/0097623 A1 | 4/2011 | Marinis, Jr. et al. |
| 2011/0100458 A1 | 5/2011 | Kang et al. |
| 2011/0162972 A1 | 7/2011 | Furuya et al. |
| 2011/0163812 A1 | 7/2011 | Bansal et al. |
| 2011/0311857 A1 | 12/2011 | Tucholski |
| 2012/0140167 A1 | 6/2012 | Blum |
| 2012/0236254 A1 | 9/2012 | Pugh et al. |
| 2013/0034760 A1 | 2/2013 | Otts et al. |
| 2013/0035760 A1 | 2/2013 | Portney |
| 2013/0108907 A1 | 5/2013 | Bhardwaj et al. |
| 2013/0122132 A1 | 5/2013 | Pugh et al. |
| 2013/0158378 A1* | 6/2013 | Berger ............... A61B 5/14546 600/348 |
| 2013/0166025 A1 | 6/2013 | Pugh et al. |
| 2013/0174978 A1 | 7/2013 | Pugh et al. |
| 2013/0203895 A1 | 8/2013 | Dershem |
| 2013/0222759 A1 | 9/2013 | Pugh et al. |
| 2013/0230774 A1 | 9/2013 | Ortega et al. |
| 2013/0258277 A1 | 10/2013 | Pugh et al. |
| 2014/0000101 A1 | 1/2014 | Pugh et al. |
| 2014/0028969 A1 | 1/2014 | Pugh et al. |
| 2014/0085599 A1 | 3/2014 | Etzkorn |
| 2014/0088372 A1* | 3/2014 | Saeedi .................. G16H 50/20 600/301 |
| 2014/0088881 A1* | 3/2014 | Saeedi .................. G16H 50/20 702/19 |
| 2014/0107445 A1 | 4/2014 | Liu |
| 2014/0320800 A1 | 10/2014 | Collins et al. |
| 2014/0327875 A1 | 11/2014 | Blum et al. |
| 2014/0340631 A1 | 11/2014 | Pugh |
| 2014/0346695 A1 | 11/2014 | Pugh et al. |
| 2014/0349005 A1* | 11/2014 | Everett ............. G01N 27/4145 427/2.13 |
| 2014/0349211 A1 | 11/2014 | Wei et al. |
| 2014/0354946 A1 | 12/2014 | Pugh et al. |
| 2015/0126834 A1* | 5/2015 | Wang .................. A61B 5/6833 600/345 |
| 2015/0323811 A1 | 11/2015 | Flitsch et al. |
| 2017/0181669 A1* | 6/2017 | Lin ..................... G01N 27/403 |

FOREIGN PATENT DOCUMENTS

| | | |
|---|---|---|
| JP | 2006274346 A | 10/2006 |
| JP | 200898099 A | 4/2008 |
| WO | 2008091859 A1 | 7/2008 |
| WO | 2011113903 A1 | 9/2011 |
| WO | 2013062662 A1 | 5/2013 |

OTHER PUBLICATIONS

"Non-ideal effects improvement of SF6 plasma treated hafnium oxide film based on electrolyte-insulator-semiconductor structure for pH-sensor application" by Lu et al., Microelectronics Reliability, vol. 50, pp. 742-746, 2010.*

U.S. Appl. No. 14/460,671, filed Aug. 15, 2014 entitled "Wafer Level Overmold for Three Dimensional Surfces".

Appendix P List of IBM Patents or Patent Applications Treated as Related.

(56) References Cited

OTHER PUBLICATIONS

Beeckman, J et al.; "Liquid-crystal photonic applications"; SPIEDigitalLibrary.org/oe; Optical Engineering; vol. 50(8); 081202; Aug. 2011; Copyright 2011 SPIE; <http://opticalengineering.spiedigitallibrary.org/on04/07/2014 Terms of Use: http://spiedl.org/terms>.

Blue Spark Technologies, "UT Series Printed Batteries", Product Information, UT Series Oct-12-2, Copyright 2012, website: <www.bluesparktechnologies.com>.

Ding, Ke-Qiang; "Cyclic Voltmmetrically-prepared MnO2 Coated on a ITO Glass Substrate"; Journal of the Chinese Chemical Society; 2009; 56; pp. 171-181.

Li, Xiaoping et al. ; "Composite of Indium and Polysorbate 20 as Inhibitor for Zinc Corrosion in Alkaline Solution"; Bull. Korean Chem. Soc.; 2012; vol. 33; No. 5.; <http://dx.doi.org/10.5012/bkcs.2012.33.5.1566>.

Ren, Hongwen et al.; "Tunable electronic lens using a gradient polymer network liquid crystal" Received Oct. 15, 2002; accepted Nov. 12, 2002' Applied Physics Letters; vol. 82; No. 1; Jan. 6, 2003.

U.S. Appl. No. 61/858,346, filed Jul. 25, 2013 entitled "Variable Focal Length Lens".

U.S. Appl. No. 61/976,595, filed Apr. 8, 2014 entitled "Thin Flexible Microsystem with Low-Profile Integrated Thin Film Battery".

U.S. Appl. No. 14/340,304, filed Jul. 24, 2014 entitled Cathode for Thin File Microbattery.

U.S. Appl. No. 14/340,343, filed Jul. 24, 2014 entitled Homogeneous Solid Metallic Anode for Thin Film Microbattery.

U.S. Appl. No. 14/340,253, filed Jul. 24, 2014 entitled Thin, Flexible Microsystem With Integrated Energy Source.

U.S. Appl. No. 14/340,164, filed Jul. 24, 2014 entitled Variable Focal Length Lens.

Badugu et al.; "A Glucose Sensing Contact Lens: A Non-Invasive Technique for Continuous Physiological Glucose Monitoring"; Journal of Fluorescence; vol. 13; No. 5; Sep. 2003; Copyright 2003; pp. 371-374.

Liao et al.,; "A 3μW Wirelessly Powered CMOS Glucose Sensor for an Active Contact Lens"; 2011 IEEE International Solid-State Circuits Conference; 978-1-61284-302-5/11; copyright 2011 IEEE; pp. 38-41.

Rolka et al.,; "Integration of a Capacitive EIS Sensor into a FIA System for pH and Penicillin Determination"; Sensors; ISSN 1424-8220; Copyright 2004 by MDPI; Sensors 2004, 4; pp. 84-94, website: <http://www.mdpi.net/sensors>.

Office Action dated Mar. 9, 2018 received in U.S. Appl. No. 14/340,343.

Office Action dated Aug. 24, 2017 received in U.S. Appl. No. 14/340,343.

"Fresnel Lens", Wikipedia, last modified Jan. 30, 2017, 9 pages, https://en.wikipedia.org/wiki/Fresnel_lens.

Notice of Allowance dated May 31, 2018 received in U.S. Appl. No. 14/340,343.

\* cited by examiner

US 10,105,082 B2

METAL-OXIDE-SEMICONDUCTOR CAPACITOR BASED SENSOR

BACKGROUND

The present invention relates generally to semiconductor devices, and more specifically a metal-oxide-semiconductor (MOS) capacitor based sensor.

The traditional MOS structure is obtained by growing a layer of silicon dioxide ($SiO_2$) on top of a silicon substrate and depositing a layer of metal or polycrystalline silicon (the latter is commonly used). As the silicon dioxide is a dielectric material, its structure is equivalent to a planar capacitor, with one of the electrodes replaced by a semiconductor.

In general, a capacitor is a passive two-terminal electrical component used to store energy electrostatically in an electric field. The forms of practical capacitors vary widely, but all contain at least two electrical conductors (plates) separated by a dielectric (i.e., insulator). The conductors can be thin films of metal, aluminum foil or disks, etc. A dielectric can be glass, ceramic, plastic film, air, paper, mica, etc. Capacitors are widely used as parts of electrical circuits in many common electrical devices. Unlike a resistor, an ideal capacitor does not dissipate energy. Instead, a capacitor stores energy in the form of an electrostatic field between its plates.

When there is a potential difference across the conductors, an electric field develops across the dielectric, causing positive charge (+Q) to collect on one plate and negative charge (−Q) to collect on the other plate. An ideal capacitor is characterized by a single constant value for its capacitance. Capacitance is expressed as the ratio of the electric charge (Q) on each conductor to the potential difference (V) between them. The SI unit of capacitance is the farad (F), which is equal to one coulomb per volt (1 C/V). Typical capacitance values range from about 1 pF ($10^{-12}$ F) to about 1 mF ($10^{-3}$ F).

SUMMARY

Aspects of an embodiment of the present invention disclose a glucose sensor. The glucose sensor comprises a conducting back electrode. The glucose sensor also comprises a silicon substrate in electrical contact with the conducting back electrode. The glucose sensor also comprises a dielectric layer disposed on the silicon substrate. The glucose sensor also comprises a pH sensing layer disposed on the dielectric layer. The glucose sensor also comprises a chemical layer disposed on the pH sensing layer, wherein the chemical layer is in contact with an aqueous solution. The glucose sensor also comprises a conductive electrode disposed on the dielectric layer, wherein the conductive electrode is in contact with the aqueous solution.

BRIEF DESCRIPTION OF THE SEVERAL VIEWS OF THE DRAWINGS

The following detailed description, given by way of example and not intended to limit the disclosure solely thereto, will best be appreciated in conjunction with the accompanying drawings, in which.

DETAILED DESCRIPTION

Figure 1:
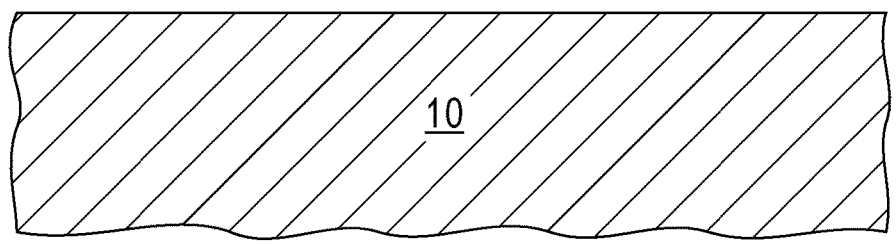
FIGS. 1-5 are cross-sectional views of a MOS capacitor based sensor depicting the basic processing steps that are used in forming the MOS capacitor based sensor.

Embodiments of the present invention recognize that current glucose sensors have high power requirements and slow response times or require optical readers and are not quantitative. Diabetes is an important worldwide health issue and the need for in-vivo glucose monitoring can be a significant advancement in the management of this disease. Fluctuation of glucose levels in blood also produce fluctuations in glucose levels in tears. Hence, glucose can be monitored by measuring glucose levels in tears by embedding sensors in a contact lens.

One type of glucose sensor, an electrochemical amperometric sensor, measures a concentration of an analyte by measuring a current generated through electrochemical oxidation or reduction reactions of the analyte at a working electrode of a sensor. A reduction reaction occurs when electrons are transferred from the electrode to the analyte, whereas an oxidation reaction occurs when electrons are transferred from the analyte to the electrode. The direction of the electron transfer is dependent upon the electrical potentials applied to the working electrode by a potentiostat. A counter electrode and/or reference electrode is used to complete a circuit with the working electrode and allow the generated current to flow. When the working electrode is appropriately biased, the output current is proportional to the reaction rate, which provides a measure of the concentration of the analyte surrounding the working electrode.

A reagent may be localized proximate the working electrode to selectively react with a desired analyte. For example, glucose oxidase can be fixed near the working electrode to react with glucose and release hydrogen peroxide, which is then electrochemically detected by the working electrode to indicate the presence of glucose. Amperometric sensors measure $2e^-$ production on the electrode coated with glucose oxidase and are based on the reaction scheme shown below, Scheme (1).

Scheme (1):

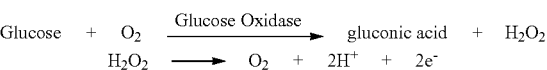

Another type of glucose sensor is optically labeled boronic acid molecules (e.g., a boronic acid containing fluorophore) embedded in a contact lens. When glucose molecules bind to the boronic acid molecules, the color of contact lens changes thereby providing a semi quantitative measure of glucose concentration.

Embodiments of the present invention propose a metal-oxide-semiconductor (MOS) capacitor based sensor suitable for embedding in a contact lens. The MOS capacitor based sensor has low power requirements and is compatible with silicon process technology. Therefore, the MOS capacitor based sensor can be easily integrated with a silicon based circuit chip.

Main components of a glucose sensing device for contact lens applications are a MOS capacitor based sensor and other silicon based circuit chips or devices for power management, signal measurement, or communication. This disclosure focuses on the MOS capacitor based sensor component.

Some examples of circuit chips or devices for power management, signal measurement, or communication are: one or more wireless antenna devices; one or more integrated power supplies such as an integrated battery, capacitor or other power source; one or more integrated energy scavenging devices; one or more external power sources; or one or more wired or wireless communication devices. For example, a power source may be a thin film battery, a radio frequency (RF) power amplifier, or any other suitable power source.

In one embodiment, the glucose sensing device (including the MOS capacitor based sensor) may be located within the thickness of a contact lens. The glucose sensing device is positioned within a contact lens such that the glucose sensing device is not in the optical region of the contact lens (e.g., the center region of the contact, a range of about 4 mm to about 10 mm in diameter, preferably about 6 mm in diameter). The glucose sensing device should be placed in the outer region of the contact lens.

In another embodiment, the glucose sensing device may be integrated in a microsystem that can serve as a platform and ecosystem for a variety of microsystems and can be embedded in a contact lens. An example of a suitable microsystem is described in U.S. patent application Ser. No. 14/340,253 filed on Jul. 24, 2014 entitled "Thin, flexible microsystem with integrated energy source," the entirety of which is incorporated by reference herein. The microsystem may include one or more thin silicon die (e.g., the glucose sensing chip), interconnect wiring, and a battery energy source. One or more circuits may be customized on the one or more silicon die to perform one or more functions.

In one embodiment, the MOS capacitor based sensor for sensing glucose concentrations comprises a material stack of Si, $SiO_2$, $HfO_2$, and glucose oxidase immobilized over the $HfO_2$ surface. The glucose sensing range of the MOS capacitor based sensor is from about 0.1 mM (millimolar) of glucose to 1 mM of glucose. Advantages of the MOS capacitor based sensor include: $HfO_2$ has near Nernst limit of pH sensitivity (60 mV/pH); pH sensitivity is not impacted by proteins in tears; and low power requirements for sensing. The energy used for sensing is about $0.5*C*V^2$ or about $1\times10^{-10}$ J, where C (capacitance) is about 200 pF and V (potential difference/voltage) is 1.

Detailed embodiments of the present invention are disclosed herein with reference to the accompanying drawings. It is to be understood that the disclosed embodiments are merely illustrative of potential embodiments of the present invention and may take various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper", "lower", "right", "left", "vertical", "horizontal", "top", "bottom", and derivatives thereof shall relate to the disclosed present invention, as oriented in the drawing figures. The terms "overlying", "underlying", "atop", "on top", "positioned on" or "positioned atop" mean that a first element, such as a first structure, is present on a second element, such as a second structure, wherein intervening elements, such as an interface structure may be present between the first element and the second element. The term "direct contact" means that a first element, such as a first structure, and a second element, such as a second structure, are connected without any intermediary conducting, insulating or semiconductor layers at the interface of the two elements.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, % by weight, and the like are synonyms that refer to the concentration of a substance as the weight of that substance divided by the weight of the composition and multiplied by 100.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The present invention will now be described in detail with reference to the figures.

Reference is first made to FIGS. 1-5 are cross-sectional views of a MOS capacitor based sensor depicting the basic processing steps that are used in forming the MOS capacitor based sensor.

In FIG. 1, semiconductor substrate 10 is provided. In one embodiment, semiconductor substrate 10 comprises Si. In other embodiments, semiconductor substrate 10 may comprise any semiconducting material including, but not limited to: Ge, SiGe, SiC, SiGeC, Ge, GaAs, GaN, InAs, InP and all other III/V or II/VI compound semiconductors. In some embodiments, semiconductor substrate 10 may also comprise an organic semiconductor or a layered semiconductor such as Si/SiGe, a silicon-on-insulator (SOI), a SiGe-on-insulator (SGOI) or germanium-on-insulator (GOI). In other embodiments, semiconductor substrate 10 may be doped, undoped or contain doped and undoped regions therein. In yet another embodiment, semiconductor substrate 10 may include a single crystal orientation or it may include at least two coplanar surface regions that have different crystal orientations (the latter substrate is referred to in the art as a hybrid substrate). Semiconductor substrate 10 is in electrical contact with a conducting electrode (e.g., the back electrode).

In other embodiments, semiconductor substrate 10 may also include a first doped (n- or p-) region, and a second doped (n- or p-) region. The first doped region and the second doped region may be the same, or they may have different conductivities and/or doping concentrations. These doped regions are known as "wells" and they are formed utilizing conventional ion implantation processes.

Figure 2:
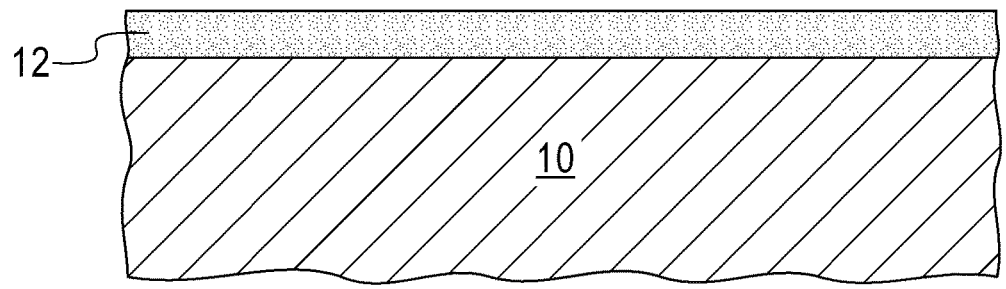

In FIG. 2, after processing semiconductor substrate 10, dielectric layer 12 is formed on the surface of semiconductor substrate 10. Dielectric layer 12 may be formed utilizing a conventional growing technique that is well known to those skilled in the art including, for example, oxidation (e.g., thermal oxidation, wet chemical oxidation, etc.) or oxynitridation. In one embodiment, dielectric layer 12 is comprised of silicon oxide (e.g., $SiO_2$). In other embodiments, dielectric layer 12 may comprise silicon oxynitride, a nitrided silicon oxide as well as other (e.g., non-Si) semiconductor oxides, oxynitrides, or nitrided oxides. The thickness of dielectric layer 12 is typically in the range of about 15 angstroms to about 45 angstroms, and the thickness is preferably about 20 angstroms.

Figure 3:
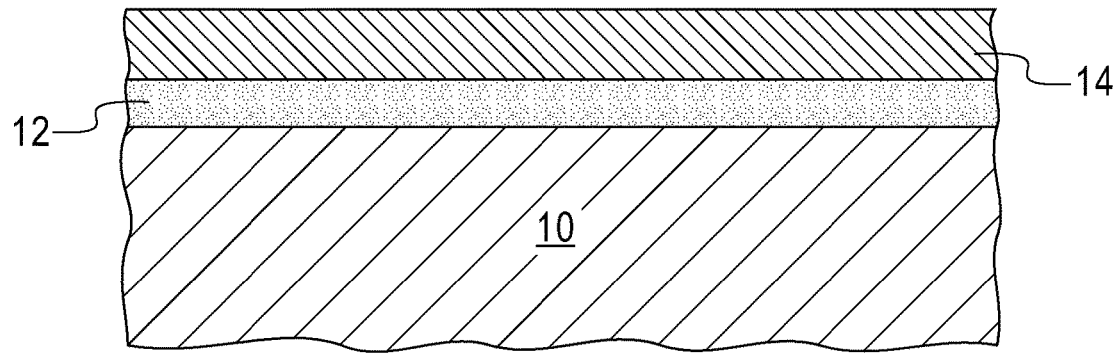

In FIG. 3, pH sensing layer 14 is formed on the surface of dielectric layer 12 by a deposition process such as, for example, chemical vapor deposition (CVD), plasma-assisted CVD, physical vapor deposition (PVP), metalorganic chemical vapor deposition (MOCVD), atomic layer deposition (ALD), evaporation, reactive sputtering, chemical solution deposition and other like deposition processes. pH sensing layer 14 may also be formed utilizing any combination of the above processes.

In one embodiment, pH sensing layer 14 is comprised of hafnium oxide ($HfO_2$). In other embodiments, pH sensing layer 14 may comprise hafnium silicate ($HfSiO_x$), Hf silicon oxynitride (HfSiON), $ZrO_2$, or $Al_2O_3$. In some embodiments, pH sensing layer 14 comprises a mixture of $HfO_2$ and $ZrO_2$. Generally, pH sensing layer 14 comprises a "high k" material whose dielectric constant is greater than about 10.0. The thickness of pH sensing layer 14 is typically in the range of about 10 angstroms to about 40 angstroms, and the thickness is preferably about 40 angstroms. The surface area of pH sensing layer 14 is in the range of about 0.001 $cm^2$ to about 0.1 $cm^2$.

Figure 4:
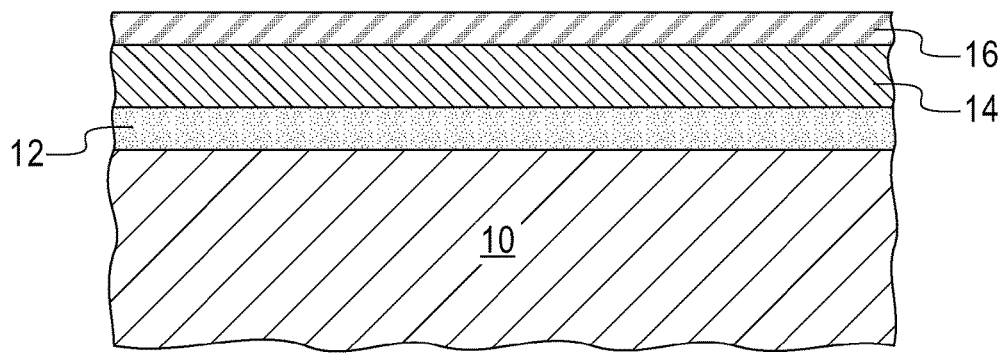

Once the structure shown in FIG. 3 is formed, an optional chemical layer 16 is formed on pH sensing layer 14 providing the structure shown in FIG. 4. In one embodiment, if the MOS capacitor based sensor is to sense glucose concentration, chemical layer 16 comprises the enzyme glucose oxidase. Chemical layer 16, comprising the enzyme glucose oxidase, can be immobilized on the surface of pH sensing layer 14. An example of an immobilization process is absorptive immobilization. In general, the absorptive immobilization process comprises preparing an enzyme solution (e.g., the enzyme dissolved in a buffer solution), disposing the solution on pH sensing layer 14, and waiting a period of time for the absorption to take place.

In other embodiments, the MOS capacitor based sensor can be used for diagnostics of other analytes in tears.

Figure 7:
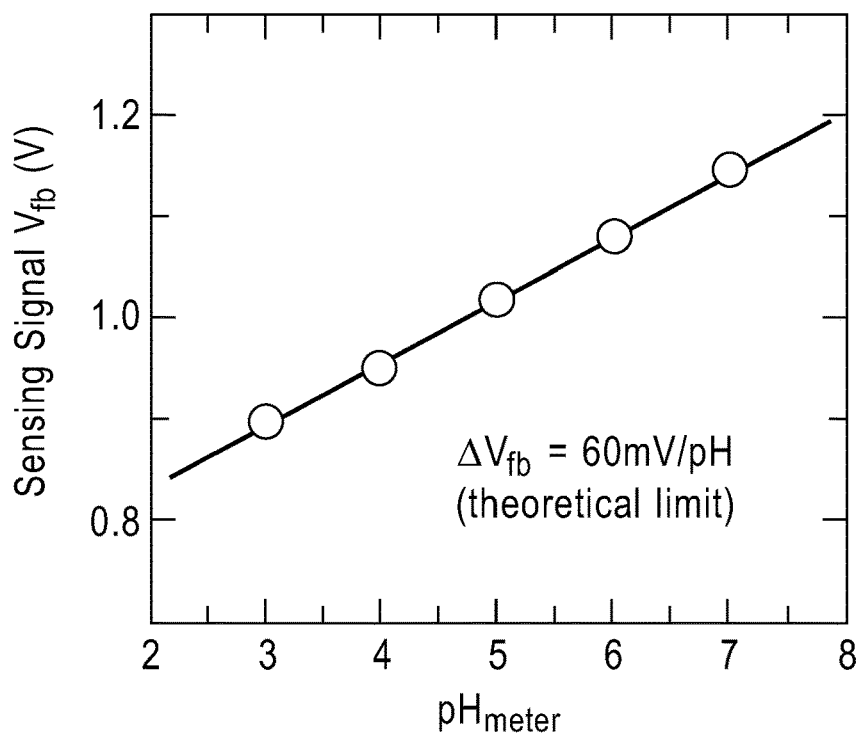
FIG. 7 depicts a plot of sensing signal $V_{fb}$ in volts versus the pH of several buffer solutions which demonstrates the pH sensitivity of the MOS capacitor based sensor.
Figure 8:
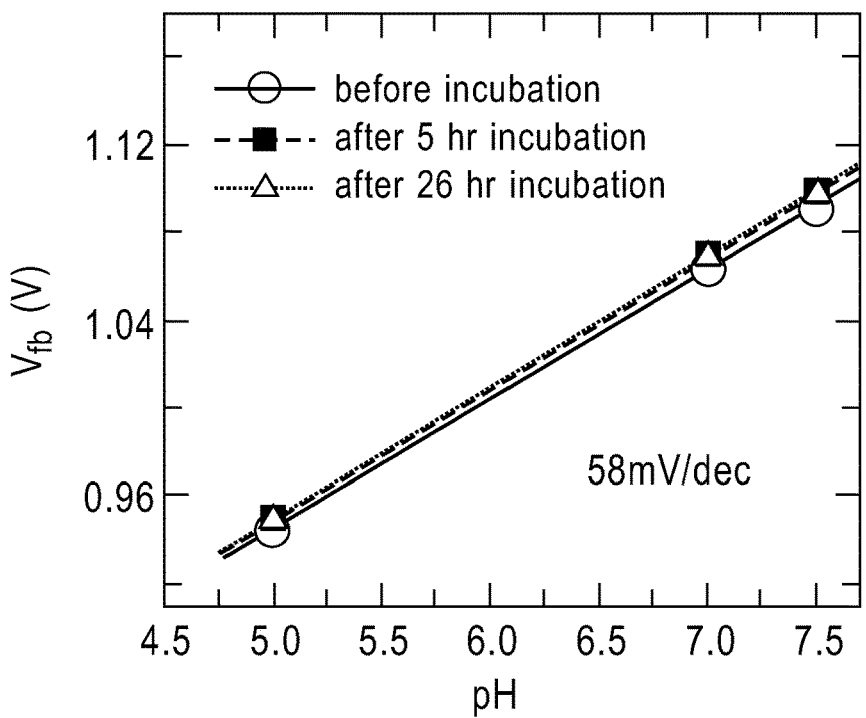
FIG. 8 depicts a plot of sensing signal $V_{fb}$ in volts versus the pH of several artificial tear solutions at different stages of incubation which demonstrates that the pH sensitivity of the MOS capacitor based sensor is not impacted by proteins in tears.
Figure 9:
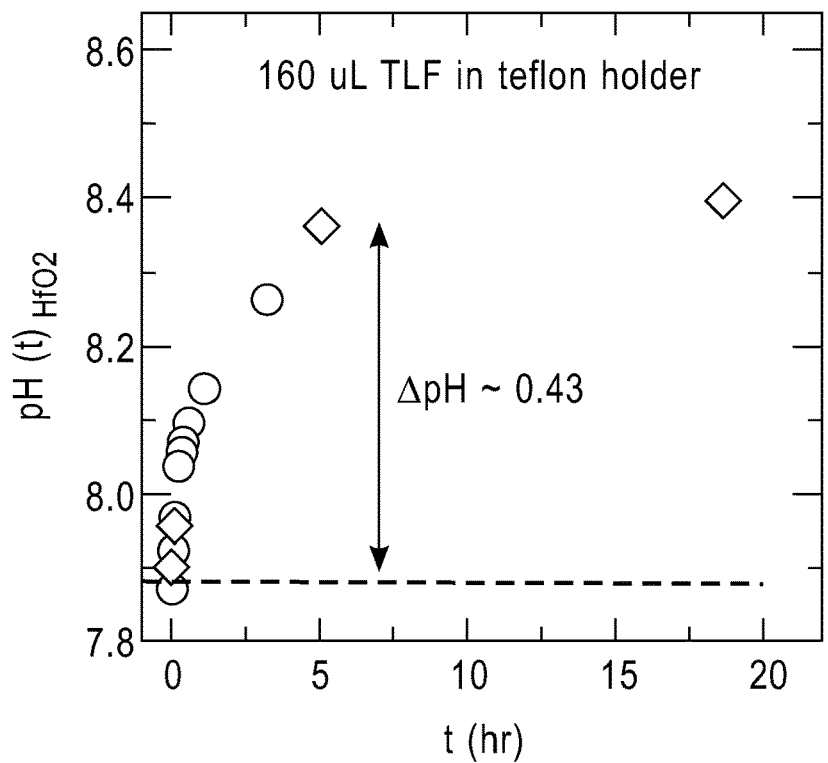
FIG. 9 depicts a plot of pH of an artificial tear solution monitored by the MOS capacitor based sensor ($HfO_2$) over time which demonstrates that the MOS capacitor based sensor can reliably measure small pH changes.

In another embodiment, if the MOS capacitor based sensor is to sense just pH changes in tears, no chemical layer is deposited on pH sensing layer 14. The pH of tears can provide diagnostics about eye infection. In order to measure the pH changes in tears, pH sensing layer 14 would be left bare (no immobilization of another layer). FIGS. 7, 8 and 9 demonstrate the pH sensitivity of pH sensing layer 14 (e.g., $HfO_2$) in buffers and in artificial tears.

In other embodiments, and if the MOS capacitor based sensor is to sense proteins in tears, chemical layer 16 comprises antibodies capable of binding to specific proteins. Some proteins present in tears may be biomarkers for certain diseases. In order to sense proteins in tears, pH sensing layer 14 (e.g., $HfO_2$) is coated with appropriate biomolecules (e.g., antibodies) that would specifically bind a target protein. The charge of the protein changes the flat band voltage which, in turn, would change the capacitance measured at a fixed voltage.

Figure 5:
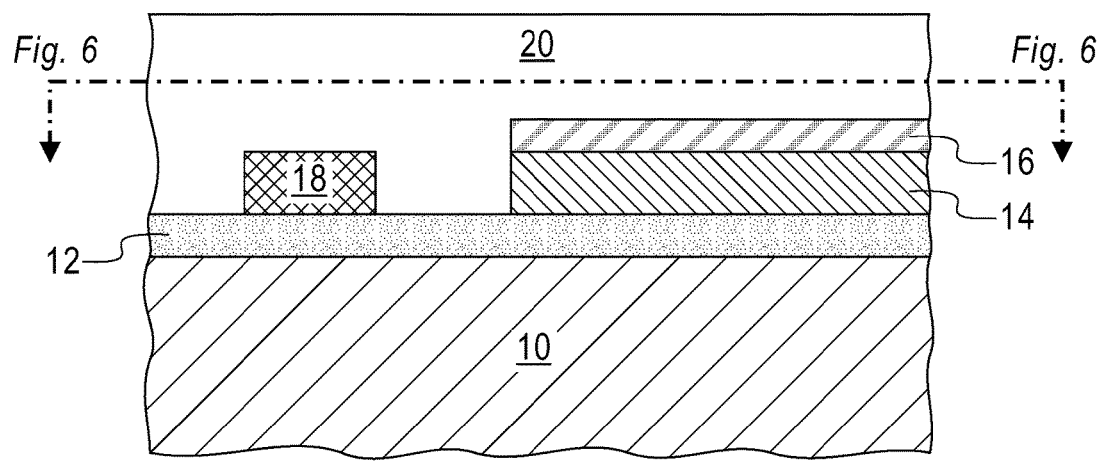

FIG. 5 depicts top electrode 18 deposited over a portion of dielectric layer 12 not covered by pH sensing layer 14. In various embodiments, top electrode 18 may comprise gold, silver-chloride, or platinum. In general, top electrode 18 may comprise gold, platinum, palladium, titanium, silver, silver-chloride, aluminum, carbon, metals, conductors formed from noble materials, combinations of these, etc. Top electrode 18 can be formed by patterning conductive materials on dielectric layer 12 (e.g., by deposition techniques, lithography techniques, etc.). FIG. 5 also depicts aqueous material 20 surrounding top electrode 18 and chemical layer 16. In one embodiment, aqueous material 20 comprises tears.

Figure 6:
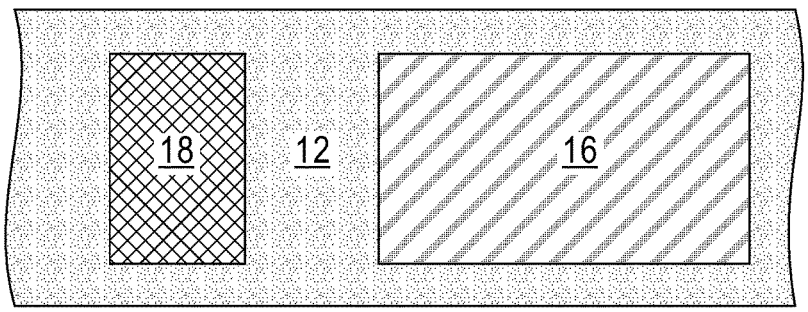
FIG. 6 depicts a top down view of a completed MOS capacitor based sensor.

FIG. 6 depicts a top down view of a completed MOS capacitor based sensor. The completed MOS capacitor based sensor shown in FIG. 6 can be fabricated utilizing conventional processes that are well known in the art, such as lithography and etching. In one embodiment, as shown, dielectric layer 12 covers the top surface of provided semiconductor substrate 10.

In one embodiment, after the MOS capacitor based sensor is completed it can be electrically connected to one or more silicon based circuit chips or devices for power management, signal measurement, or communication. For example, a substrate is provided that is suitable for mounting the MOS capacitor based sensor and any other silicon based circuit chips or devices needed for the sensor to function. The substrate can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc. to create electrodes, interconnects, antennae, etc. The substrate can be a relatively rigid material, such as polyethylene terephthalate ("PET") or another material sufficient to structurally support the circuitry and/or electronics when integrated in a contact lens.

In one embodiment, substantially transparent conductive materials (e.g., indium tin oxide (ITO)) can be patterned on the substrate to form circuitry, electrodes, etc. In other embodiments, those skilled in the art understand that other transparent conducting oxides can be used, such as indium zinc oxide (IZO), Al-doped zinc oxide (AZO), Ga-doped zinc oxide (GZO), or indium gallium zinc oxide (IGZO). In other embodiments, any combination of ITO, IZO, AZO, GZO, and IGZO can be used. In another embodiment, a conducting polymer or any other transparent conductive material may be used. Interconnects between the MOS capacitor based sensor and any other silicon based circuit chips or devices needed for the sensor to function can be formed by depositing suitable patterns of conductive materials on the substrate. A combination of resists, masks, and deposition techniques can be employed to pattern materials on the substrate.

Examples of silicon based circuit chips or devices need for the sensor to function may include a power source, a controller, or a communication device.

A power source may be a thin film battery, a radio frequency (RF) power amplifier, solar cells (photovoltaic cells), inertial power scavenging system, or any other suitable power source. The power source may be configured to provide any power needed to the MOS capacitor based sensor or any other silicon based circuit chips or devices need for the sensor to function.

A controller may contain logic that operates the MOS capacitor based sensor and a communication device. The communication device may be a radio frequency signal generator (e.g., RFID tag) or an antenna. In one embodiment, the controller may modulate the impedance of an antenna in a manner that is perceivably by an external reader. In another embodiment, if the communication device is an RFID tag, RFID tags can be either passive, active, or battery-assisted passive. An active tag has an on-board battery and periodically transmits its ID signal. A battery-assisted passive (BAP) has a small battery on board and is activated when in the presence of an RFID reader. Tags may be read/write, where object-specific data can be written into the tag by the system user. RFID tags contain at least two parts: an integrated circuit for storing and processing information, modulating and demodulating a radio-frequency (RF) signal, collecting DC power from the incident reader signal, and other specialized functions; and an antenna for receiving and transmitting the signal. The tag information is stored in a non-volatile memory. The RFID tag includes either a chip-wired logic or a programmed or programmable data processor for processing the transmission and sensor data, respectively.

In another embodiment, after the MOS capacitor based sensor is completed it can be integrated along with one or more silicon based circuit chips for power management, signal measurement, or communication in a suitable microsystem is described in U.S. patent application Ser. No. 14/340,253 filed on Jul. 24, 2014 entitled "Thin, flexible microsystem with integrated energy source."

After the MOS capacitor based sensor is completed and electrically connected to one or more silicon based circuit chips or devices for power management, signal measurement, or communication, the MOS capacitor based sensor and the one or more silicon based circuit chips or devices are embedded in a contact lens.

A contact lens is composed of lens material and includes two surfaces, an outer surface and an inner surface, both of which are spherical. In one embodiment, the inner surface is concave and the outer surface convex and opposite the inner surface. The lens material is porous. The MOS capacitor based sensor and the one or more silicon based circuit chips or devices are located within the thickness of the contact lens. In one embodiment, the MOS capacitor based sensor and the one or more silicon based circuit chips or devices, are positioned within the contact lens such that the MOS capacitor based sensor and the one or more silicon based circuit chips or devices are not in the optical region of the contact lens (e.g., the center region of the contact, a range of about 4 mm to about 10 mm in diameter, preferably about 6 mm in diameter). The MOS capacitor based sensor and the one or more silicon based circuit chips or devices should be placed in the outer region of the contact lens.

The particular dimensions (including dimensions attributable to thickness, diameter, curvature, and etc.) of the contact lens may vary. Lenses are classified by the curvature of the two optical surfaces. Therefore, in other embodiments, the contact lens may one of the following: biconvex (or double convex, or just convex) if both surfaces are convex; equiconvex, if both surfaces have the same radius of curvature; biconcave (or just concave) if the lens has two concave surfaces; if one of the surfaces is flat, the contact lens is plano-convex or plano-concave depending on the curvature of the other surface; convex-concave or meniscus, if the contact lens has one convex side and one concave side; or any other type of contact lens.

Lens material can include any suitable material that provides support for the MOS capacitor based sensor and the one or more silicon based circuit chips or devices, contain the MOS capacitor based sensor and the one or more silicon based circuit chips or devices, and/or otherwise form a structural and/or functional body of the contact lens. Lens material may also be porous to tears in order for the sensor to come in contact with the tears. Lens material is substantially transparent, with a transmittance of 40% to 99%, preferably 70% to 99%, and biocompatible. In one embodiment, lens material may comprise a soft polymer material including but not limited to, a hydrogel, a silicone based hydrogel, a polyacrlyamide, or a hydrophilic polymer. In other embodiments, lens material may comprise polyethylene terephthalate ("PET"), polymethyl methacrylate ("PMMA"), polyhydroxyethylmethacrylate (polyHEMA) based hydrogels, or combinations thereof. I yet another embodiment, lens material may comprise a rigid gas permeable material. In yet another embodiment, lens material may comprise glass, plastic (such as a polycarbonate), or any other suitable material.

FIG. 7 through 11 demonstrate the pH sensitivity and the glucose sensing ability of the MOS capacitor based sensor.

The process for the MOS capacitor based sensor to determine the glucose level in tears includes three general steps. First, chemical layer 16 is formed on pH sensing layer 14 ($HfO_2$) providing the structure shown in FIG. 4. Chemical layer 16 comprises the enzyme glucose oxidase. Glucose reacts with $O_2$ in the presence of the enzyme glucose oxidase to produce ions ($H^+$) which cause a localized change in pH ($\Delta pH$). A voltage is applied to measure the capacitance change due to the pH change. pH sensing layer 14 ($HfO_2$) detects this $\Delta pH$ which is proportional to glucose concentration.

The MOS capacitor based sensor detects variations in the H+ ion concentration resulting from the reaction of glucose with $O_2$ in the presence of the enzyme glucose oxidase. A resulting local pH increase near pH sensing layer 14 ($HfO_2$) leads to a change in the capacitance of the MOS capacitor based sensor, which in turn leads to a change in the sensing signal (voltage) across the MOS capacitor based sensor. The change in capacitance of the MOS capacitor based sensor is caused by the $H^+$ ions changing the surface potential of pH sensing layer 14 ($HfO_2$) causing the flat band voltage to shift with a concomitant change in the capacitance measured at a fixed voltage. When the capacitance increases the sensing signal (voltage) across the MOS capacitor based sensor decreases.

The energy used for sensing is about $0.5*C*V^2$ or about $1\times10^{-10}$ J, where C (capacitance) is about 200 pF and V (potential difference/voltage) of 1 applied across the MOS capacitor based sensor from a conducting electrode (e.g., the back electrode) electrically connected to silicon substrate 10 to top electrode 18.

Second, a calibration process is completed. Capacitance is measured at a fixed voltage (near flat band) as a function of glucose concentration, thereby creating a calibration curve.

Third, a measurement is taken. To measure glucose concentration, measure the capacitance of the MOS capacitor based sensor at the fixed voltage (same as voltage used for calibration). Using the calibration curve, the glucose concentration in the tears is estimated from the measured capacitance.

FIG. 7 depicts a plot of $V_{fb}$ (flat band) in volts versus the known pH of several buffer solutions which demonstrates the pH sensitivity of the MOS capacitor based sensor. The plot in FIG. 7 shows the $V_{fb}$ (voltage flat band) in volts increasing as the pH of buffer solutions decrease (e.g., the solution is more basic). This plot shows that the MOS capacitor based sensor has a different $V_{fb}$ based on the pH of the buffer solution in contact with pH sensing layer 14.

FIG. 8 depicts a plot of $V_{fb}$ in volts versus the pH of several artificial tear solutions at different stages of incubation which demonstrates that the pH sensitivity of the MOS capacitor based sensor is not impacted by proteins in tears. The plot in FIG. 8 shows the $V_{fb}$ (voltage flat band) in volts increasing as the pH of artificial tear solutions (including lipids and proteins) decrease (e.g., the solution is more basic). This plot shows three different sets of measurements: one where the artificial tear solutions with different pH's were not incubated; one where the artificial tear solutions with different pH's were incubated for 5 hours; and one where the artificial tear solutions with different pH's were incubated for 26 hours. The three different sets of measurements a virtually the same indicating that the pH sensitivity of the MOS capacitor based sensor is not impacted by proteins in tears.

FIG. 9 depicts a plot of pH of an artificial tear solution monitored by the MOS capacitor based sensor ($HfO_2$) over time which demonstrates that the MOS capacitor based sensor can reliably measure small pH changes.

Figure 10:
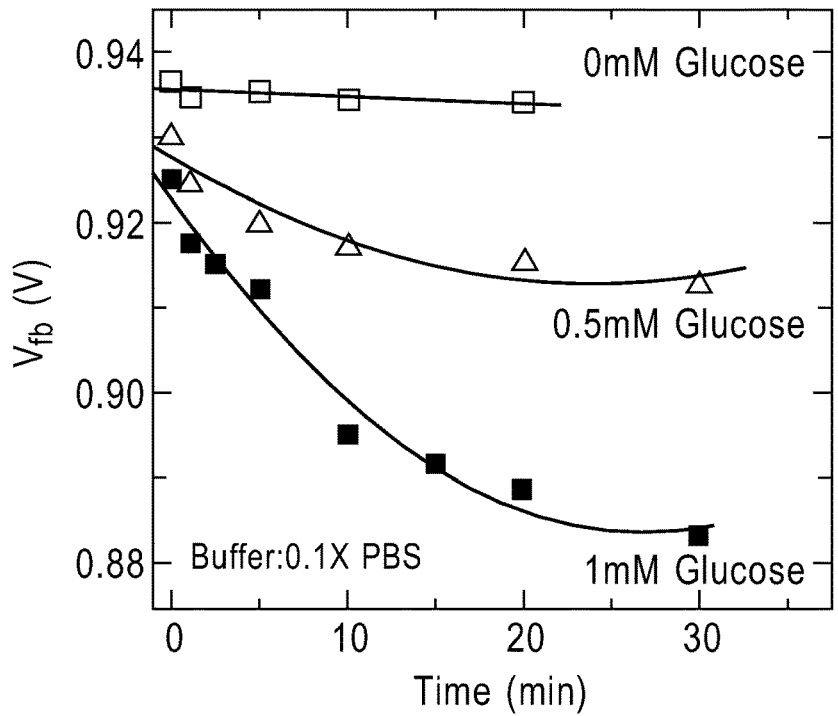
FIG. 10 depicts a plot of sensing signal $V_{fb}$ in volts over time of 3 phosphate buffer solutions each with a different concentration of glucose which demonstrates the glucose sensing ability of the MOS capacitor based sensor.

FIG. 10 depicts a plot of $V_{fb}$ in volts over time of 3 phosphate buffer solutions each with a different concentration of glucose which demonstrates the glucose sensing ability of the MOS capacitor based sensor. The measurements in this plot were performed using a phosphate buffer solution with dissolved glucose oxidase (10 units). The plot in FIG. 10 shows the $V_{fb}$ (voltage flat band) in volts over time for three solutions each with a different concentration of glucose. This plot shows that over time the higher the glucose concentration of a solution the lower the $V_{fb}$ (voltage flat band) in volts.

Figure 11:
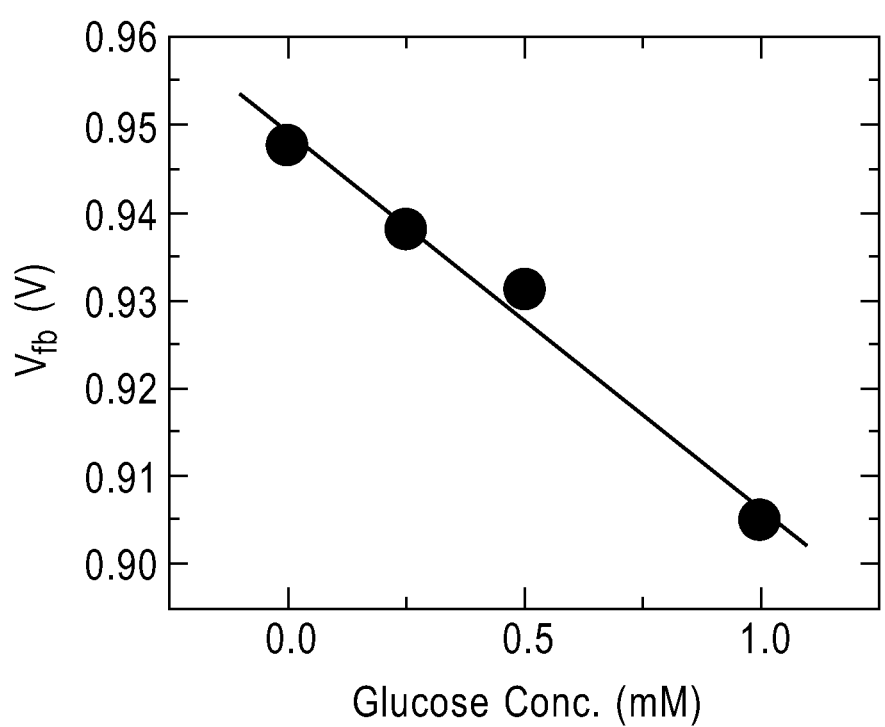
FIG. 11 depicts a calibration curve of sensing signal $V_{fb}$ in volts versus glucose concentration in mM.

FIG. 11 depicts a calibration curve of $V_{fb}$ in volts versus glucose concentration in mM.

Having described embodiments of a MOS capacitor based sensor (which are intended to be illustrative and not limiting), it is noted that modifications and variations may be made by persons skilled in the art in light of the above teachings. It is therefore to be understood that changes may be made in the particular embodiments disclosed which are within the scope of the present invention as outlined by the appended claims.

What is claimed is:
1. A glucose sensor, comprising:
   a conducting back electrode;
   a semiconductor substrate containing a semiconductor material having semiconducting properties and in electrical contact with the conducting back electrode;
   a dielectric layer disposed on the semiconductor substrate;
   a pH sensing layer disposed on a topmost surface of the dielectric layer;
   a chemical layer disposed on the pH sensing layer, wherein the chemical layer is configured to be in contact with an aqueous solution; and
   a conductive electrode disposed on the dielectric layer and laterally spaced apart from the pH sensing layer and the chemical layer, wherein the conductive electrode is configured to be in contact with the aqueous solution and has a bottommost surface that is coplanar with a bottommost surface of the pH sensing layer.

2. The glucose sensor of claim 1, wherein a sensing signal voltage between the conducting back electrode and the conductive electrode varies based on a pH change on the pH sensing layer.

3. The glucose sensor of claim 1, wherein the pH sensing layer comprises hafnium oxide ($HfO_2$).

4. The glucose sensor of claim 1, wherein the pH sensing layer comprises one or more of hafnium silicate ($HfSiO_x$), Hf silicon oxynitride (HfSiON), $ZrO_2$, or $Al_2O_3$.

5. The glucose sensor of claim 1, wherein the chemical layer comprises glucose oxidase.

6. The glucose sensor of claim 1, wherein the aqueous solution is a tear.

7. The glucose sensor of claim 5, wherein the glucose oxidase causes glucose to react with $O_2$ molecules to change a concentration of $H^+$ ions in the aqueous solution.

8. The glucose sensor of claim 2, wherein the pH change on the pH sensing layer causes a change in capacitance of the glucose sensor.

9. The glucose sensor of claim 8, wherein the change in capacitance is related to a concentration of glucose in the aqueous solution.

10. The glucose sensor of claim 5, wherein the glucose oxidase is a porous layer.

11. The glucose sensor of claim 1, further comprising a contact lens in which the glucose sensor resides.

12. A contact lens, comprising:
    a first surface with a first curvature;
    a second surface with a second curvature;
    lens material disposed between the first and second surfaces, wherein the lens material is porous; and
    a glucose sensor disposed within the lens material, said glucose sensor comprising:
        a conducting back electrode;
        a semiconductor substrate containing a semiconductor material having semiconducting properties and in electrical contact with the conducting back electrode;
        a dielectric layer disposed on the semiconductor substrate:
        a pH sensing layer disposed on the dielectric layer;
        a chemical layer disposed on the pH sensing layer, wherein the chemical layer is configured to be in contact with an aqueous solution; and
        a conductive electrode disposed on the dielectric layer and laterally spaced apart from the pH sensing layer and the chemical layer, wherein the conductive electrode is configured to be in contact with the aqueous solution and has a bottommost surface that is coplanar with a bottommost surface of the pH sensing layer.

13. The contact lens of claim 12, wherein the glucose sensor is disposed within the lens material such that the glucose sensor is not in an optical region of the contact lens.

14. The contact lens of claim 12, further comprising a device for sensing signal measurement electrically connected to the glucose sensor.

15. The contact lens of claim 12, further comprising a communication device electrically connected to the glucose sensor.

16. The contact lens of claim 12, further comprising a power source electrically connected to the glucose sensor.

17. A sensor comprising:
  a conducting back electrode;
  a semiconductor substrate containing a semiconductor material having semiconducting properties and in electrical contact with the conducting back electrode;
  a dielectric layer disposed on the semiconductor substrate;
  a pH sensing layer disposed on the dielectric layer, wherein the pH sensing layer is configured to be in contact with an aqueous solution; and
  a conductive electrode disposed on the dielectric layer and laterally spaced apart from the pH sensing layer, wherein the conductive electrode is configured to be in contact with the aqueous solution and has a bottommost surface that is coplanar with a bottommost surface of the pH sensing layer.

* * * * *